United States Patent [19]

Orlowski et al.

[11] Patent Number: 4,579,904

[45] Date of Patent: Apr. 1, 1986

[54] DIACRYLIC AND DIMETHACRYLIC ESTERS AND THEIR USE

[75] Inventors: Jan A. Orlowski, Altadena; David V. Butler, W. Covina, both of Calif.

[73] Assignee: Blendax Werke R. Schneider GmbH & Co., Mainz, Fed. Rep. of Germany

[21] Appl. No.: 558,789

[22] Filed: Dec. 7, 1983

Related U.S. Application Data

[62] Division of Ser. No. 422,727, Sep. 24, 1982, abandoned.

[51] Int. Cl.⁴ .............................................. C08L 55/00
[52] U.S. Cl. ..................................... 524/554; 524/854
[58] Field of Search ................................. 524/554, 854

[56] References Cited

U.S. PATENT DOCUMENTS 4,172,951 10/1979 Gruber et al. ..................... 560/84

Primary Examiner—Joseph L. Schofer
Assistant Examiner—Bernard Lipman
Attorney, Agent, or Firm—Jordan B. Bierman

[57] ABSTRACT

The present invention relates to a method of binding particles, in particular dental filling materials, comprising incorporating into the materials at least one compound selected from the group of diacrylic and dimethacrylic acid esters of the general formula

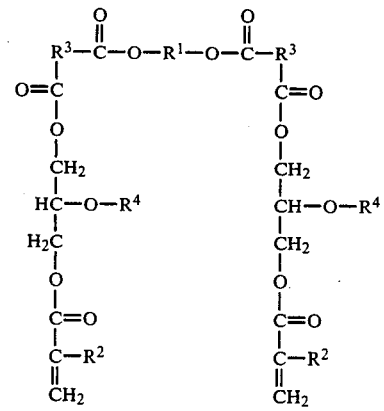

wherein $R^1$ is a divalent araliphatic, cycloaliphatic or aromatic group having 2 to 18 carbon atoms; $R^2$ is hydrogen or methyl; $R^3$ is a —CH=CH— or —(CH$_2$)$_n$— wherein n is 2 to 4, a substituted, unsubstituted or hydrogenated benzene group, cyclohexane, or cis-norbornene group and $R^4$ is H or

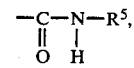

wherein $R^5$ is n-butyl, isobutyl, hexyl, substituted or unsubstituted phenyl or cyclohexyl. Dental restoratives and filling materials are also disclosed.

3 Claims, No Drawings

DIACRYLIC AND DIMETHACRYLIC ESTERS AND THEIR USE

This application is a divisional of Ser. No. 422,727, filed Sept. 24, 1982, now abandoned.

Our invention is related to new, polymerizable di(-meth)acrylic compounds and their use in binding agents, especially dental materials as well as a dental restoring and filling material containing these new compounds.

There are existing numerous polymerizable compounds having more than one double bond in the molecule. These compounds are used for various purposes, especially as binding agents for the preparation of different adhesives, a.o. in medicine and dentistry, for the preparation of dental cements, dental restoring and filling materials, dental sealing materials, orthopedic and orthodontic adhesives, etc.

We have now found that a new class of monomers being prepared by reaction of aliphatic, aromatic or cycloaliphatic dicarboxylic acid anhydrides with diols and glycidyl(meth)acrylate and carbamates thereof are particularly suitable as binding agents and adhesives, especially in the above mentioned areas.

Thus, object of our invention are new compounds of the general formula

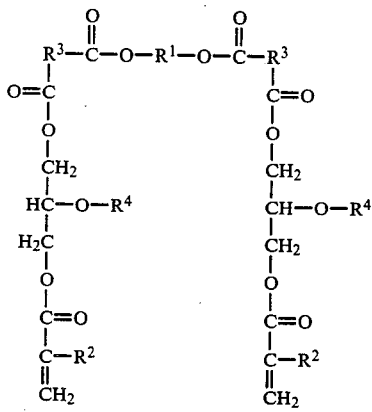

where $R^1$ is a divalent (ar)aliphatic, cycloaliphatic, or aromatic group with 2 to 18 carbon atoms, $R^2$ is H or a methyl group, $R^3$ is a —CH=CH—, —CH$_2$CH$_2$—, —CH$_2$CH$_2$CH$_2$—, —CH$_2$CH$_2$CH$_2$CH$_2$—, optionally substituted or hydrogenated benzene group, or a cyclohexane, cyclohexene, or a cisnorbornene group, and $R^4$ is H or

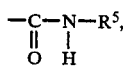

whereby $R^5$ is a n-butyl, isobutyl, hexyl, optionally substituted phenyl, or cyclohexyl group.

The residue $R^1$ especially means an ethylene, propylene, butylene, or hexamethylene group, a phenylene, a toluylene, a methylenebisphenyl, a propylenbisphenyl, a cyclohexane, a dicylopentane dimethylene, a tricyclodecane dimethylene, or a methylenebiscyclohexyl, or a propylenebiscyclohexyl group.

$R^2$ is a hydrogen atom or a methyl group; the methacrylic compound is preferred.

$R^3$ especially stands for a —CH=CH— group (derived from maleic acid), a benzene group (derived from phthalic acid), a tetrahyrobenzene group (derived from 4-cyclohexene 1,2-dicarboxylic acid), a cyclohexane group (derived from cyclohexane 1,2-dicarboxylic acid), or a cis-norbornene group (derived from cis-norbornene dicarboxylic acid), however, e.g. also malonic acid, succinic acid, glutaric acid, and adipic acid compounds are suitable.

$R^4$ is hydrogen or a carbamic acid residue

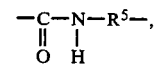

whereby $R^5$ may be a n- or isobutyl, hexyl, an optionally substituted phenyl or cyclohexyl residue.

The preparation of the new polymerizable compounds according to our invention may be effected by the following procedure:

An anhydride of an aliphatic, cycloaliphatic or aromatic dicarboxylic acid is esterified with an aliphatic, aromatic or cycloaliphatic diol, preferably at temperatures between about 120° to about 170° C.

Then this ester is reacted with glycidyl acrylate or glycidyl, methacrylate to the corresponding 3-(meth)-acroyl 2-hydroxpropyl ester.

This product may be reacted with an isocyanate at about 40° to about 100° C. in the presence of a known catalyst to give the corresponding carbamates.

British Published Patent Specification No. 2,079,297 discloses a curable dental filling material containing as resin components reaction products from diisocyanates and hydroxyalkyl diacrylates and dimethacrylates of the general formula

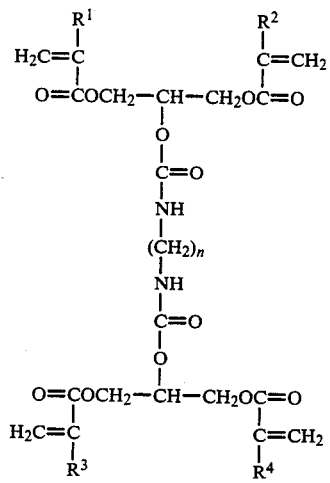

where $R^1$, $R^2$, $R^3$ and $R^4$ are hydrogen or a methyl group, and n is a number from 2 to 10.

However, the improvement of the properties of the cured dental filling materials containing such monomers does not meet the requirements of the dental practice, especially as relates to mechanical properties, particularly the hardness.

The products according to our invention are principally suitable for all those uses where monomers with more than one polymerizable double bond in the molecule are used. As previously indicated, they are especially suitable for use in medicine and dentistry.

In the last years, in dentistry the so-called "composites" have got increasing importance, as these products are easy and safe to apply by the dentist and are tolerated well by the patients. They are approaching the aim to remove the amalgam filling materials being criticized for physiological reasons.

These composites usually are composed of inorganic filling materials and polymerizable compounds.

Disadvantages of composites compared with conventional filling materials are their susceptibility to abrasion and shrinkage and their water-absorption. Secondary caries may be the result caused by the possible shrinkage between the border of the cavity and the filling in the tooth.

Therefore, those skilled in the art have made serious attempts to prepare composites having no or at least a low degree of shrinkage, a low water sorption, good mechanical properties, especially as relates to hardness, and are color-stable.

These properties may be performed by a high percentage of inorganic filling material in the filling compositions. However, the maximum filler portion is related to the properties of the monomers being present in the composition.

Conventional composites being on the market generally have the following mechanical properties after curing.

water absorption at 37° C.: 0.7–1.2 mg/cm$^2$
Compressive strength: 30,000 to 40,000 psi
Diametral tensile strength: 3,480 to 4,200 psi
Hardness (Barcol): 98
Color stability: No discoloration detectable
Determined according to ADA Specification No. 27 (Journal of the American Dental Association, Vo. 94 (June 1977)).

We have now found that these above referred mechanical properties of conventional, well-known composites may be considerably improved by use of the new monomers according to our invention which is probably caused by a considerable increase of the ratio of inorganic filler content to resin. This causes an improvement of the physical properties of the cured fillings, especially as regards to hardness and abrasion resistance.

The filler content in the filling compositions according to the invention may be increased until up to about 90%.

Therefore, it is an object of our invention to prepare a dental filling material being characterized by a portion of at least one of the new monomers according to the invention, at least one inorganic filler, a polymerization initiator or accelerator as well as optionally further compounds being well-known in those compositions such as other monomers, UV-absorbers, stabilizers, colors and dyes, etc.

The used inorganic fillers may be X-ray transparent or X-ray opaque. Suitable examples are the different silicas such as glass (pulverized glass), quartz, borosilicate glass, and other glasses like quartzite, cristobalite, etc.. Suitable X-ray opaque fillers are bariumaluminium silicate, lithium-aluminum silicate, or glass ceramic fillers containing, e.g., the elements lanthanum or zirconium. Suitable X-ray opague fillers are for example, disclosed in U.S. Pat. Nos. 3,801,344, 3,808,170 and 9,975,203 as well as in German Published Patent Specification No. 2,347,591.

To improve the compatibility of the inorganic filling material with the organic monomers the fillers may be silanized as well known in the art.

The particle diameters of the inorganic fillers are normally between at about 0.01 and 100 microns. In many cases it is possible and also suitable to use combinations of fillers with high and low particle diameters, whereby the preferred particle diameter is between about 0.05 and about 50, especially about 20 microns.

Suitable fillers are also described in our co-pending applications, Ser. No. 304,647 of Sept. 23, 1981, now U.S. Pat. No. 4,427,799, and Ser. No. 368,743, of Apr. 15, 1982, now U.S. Pat. No. 4,388,069.

In principle, composites are used in two modifications, either as two-phase compositions or as one-phase compositions.

In the two-phase compositions, one phase is containing a polymerization initiator, e.g. a peroxide, and the other phase contains an accelerator, e.g. an organic amine. Both phases are brought together shortly before the filling of the tooth is effected; the polymerization (curing) is carried out in the open cavity fitted with a bonding or reliner material, resp.

One-phase preparations are polymerizing under the influence of light, for example UV or laser light, and contain a photopolymerization initiator and optionally an accelerator therefore.

Of course, the use of the new monomers according to the invention is possible in both, two-phase and one-phase preparations.

As mentioned, one-phase preparations are polymerized by the influence of light. Suitable photopolymerization initiators are well-known: Preferred compounds for this purpose are carbonyl compounds, especially benzil and benzil derivatives like 4,4-oxidibenzil or other dicarbonyl compounds, e.g. diacetyl, 2,3-pentandione, or metal carbonyls, quinones and their derivatives. The proportion of photopolymerization initiators in the whole composition is from about 0.01 to about 5% by weight.

These one-phase preparations preferably contain also so-called polymerization accelerators. These are substances which accelerate the polymerization reaction in the presence of polymerization initiators.

Well-known accelerators are, for example, different amines such as p-toluidine, dimethyl p-toluidine, trialkyl amines, polyamines like N,N,N',N'-tetraalkyl alkylenediamines and sulfimides, preferably in an amount from about 0.01 to about 5% of the whole composition.

If the dental restoring material containing the new monomers according to the invention shall not be light-curable and be present in two phases being separated until their application, one of these mixtures contains a polymerization initiator.

These are preferably peroxides forming radicals when initiating the polymerization of the unsaturated compounds. Usual peroxides are, for example, aryl peroxides like benzoyl peroxide, cumene hydroperoxide, urea peroxide, tert.-butyl hydroperoxide, or perbenzoates and silyl peroxides, preferably in an amount of 0.01 to about 5, especially about 0.5 to about 2.5% by weight of the whole composition.

If one phase of the two-phase material contains a polymerization initiator it is suitable to add an accelerator of the above desribeed type, preferably an amine, to the other phase.

In the dental restoring materials containing the new monomers of our invention polymerizable organosilicon compounds may be used, such as methacroyl alkyl trihydroxysilanes or methacroyl trimethoxysilane, to improve the adhesion between inorganic filler and resin.

In addition to the new monomers according to the invention other monomers already proposed for this purpose may be used in dental restoring materials. Such monomers are, for example, alkanediol dimethacrylates like 1,6-hexanediol dimethacrylate, 1,4-butanediol dimethacrylate, or tri- or tetraethyleneglycol dimethacrylate, bis-(2-methacroylethyl) phthalate, isophthalate or terephthalate, trimethylolpropane di- and trimethacrylate, reaction products from diisocyanates and simple hydroxyalkyl methacrylates as described, e.g., in German Published Patent Application No. 2,312,559, reaction products from bisphenols, particularly Bisphenol A, and glycidyl methacrylate (Bis-GMA), adducts from (di)isocyanates and 2,2-propane bis-3-(4-phenoxy)-1,2-hydroxypropane-1-methacrylate according to U.S. Pat. No. 3,629,187, and other suitable polymerizable compounds already disclosed for this purpose.

Suitable monomers are also the adducts from methacroylalkyl ethers, alkoxybenzenes and alkoxycycloalkanes, resp., and diisocyanates disclosed in European Published Patent Application No. 44,352.

Composite materials may contain low amounts of suitable dyestuffs to adjust the color of the fillings as natural as possible.

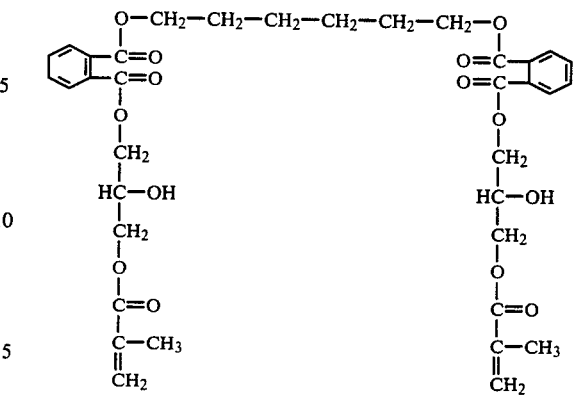

Refraction index (30° C.): 1.525.

Corresponding acrylic compounds are prepared in an analogous way.

(b) This compound may be reacted with n-butyl isocyanate in the presence of dibutyl tindiacetate at 70°–80° C. for 3 hours to give the corresponding di n-butyl carbamate of the formula

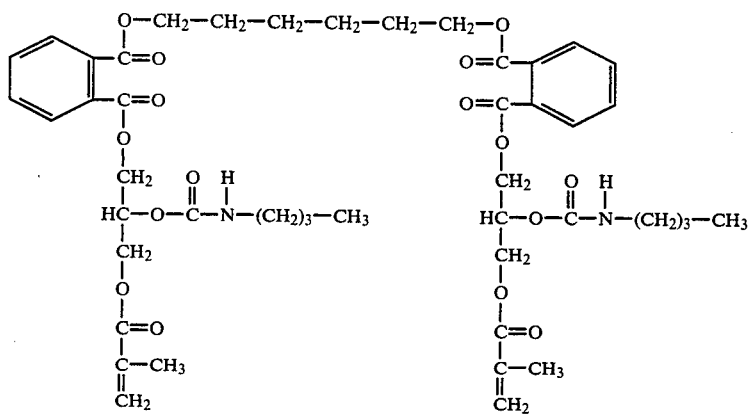

It may be also useful to in clude low amounts of UV stabilizers, for example hydroquinone, p-benzoquinone, tert.-butyl hydroxytoluene, etc..

The following examples will illustrate our invention:

EXAMPLE A (a) 148 g phthalic anhydride, 0.1 g 2,5-di-tert.-butyl-4-methyl phenol and 59 g 1,6-hexanediol are heated for 2 hours at 140° C. under stirring on a reflux condenser. Then, 160 g glycidyl methacrylate are added during 1 hour while keeping the temperature at 130° C. Thereafter, the temperature was maintained at 130° C. until the acid number of the mixture was below 0.5. Then, the unreacted glycidyl methacrylate was removed under 110 mm Hg pressure in the vacuum. Complete removal is controlled by determination of the epoxy equivalent value. The reaction product thus obtained is a colourless, viscous liquid of the structure Refraction index (30° C.): 1.512.

Similarly prepared were the corresponding acrylic compounds.

EXAMPLE B (a) According to the procedure described in Example A. (a), 1,3-butylenbis [2-(3'-methacroyl-2'-hydroxypropyl)phthalate] as prepared from 1,3-butanediol, phthalic anhydride and glycidyl methacrylate:

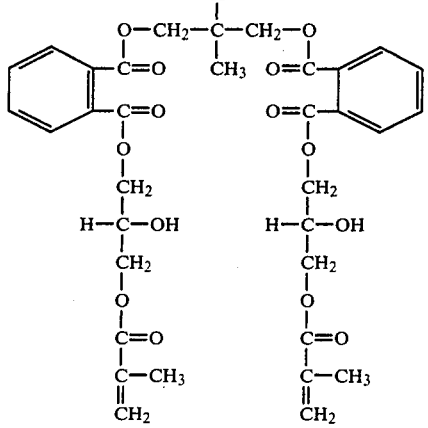

Refraction index (25° C.): 1.525

(b) To 226 g of the substance prepared according to (a) 0.15 g dibutyl tindiacetate, 79.3 g phenyl isocyanate where added under stirring during 1 hour at 70°–80° C. The corresponding diphenyl carbamate was produced in quantitative yield:

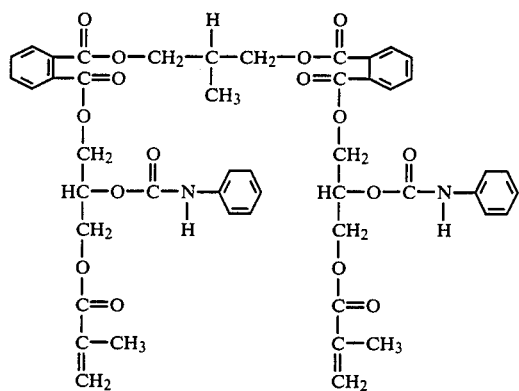

Refraction index (70° C.): 1.535

Also prepared were the corresponding acrylic compounds.

EXAMPLE C (a) 1,4-Cylohexanebis-(3'-methacroyl-2'-hydroxypropyl maleate) is prepared according to the general procedure described in Example A. (a) from maleic anhydride, 1,4-cyclohexanediol, and glycidyl methacrylate:

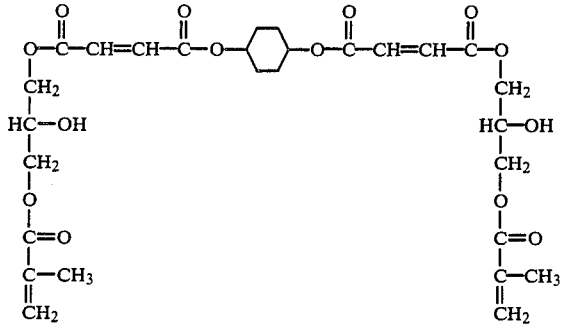

Refraction index (50° C.): 1.495

(b) The substance prepared according to (a) was reacted with phenyl isocyanate according to the general method described in Example B. (b) to yield the corresponding diphenyl carbamate:

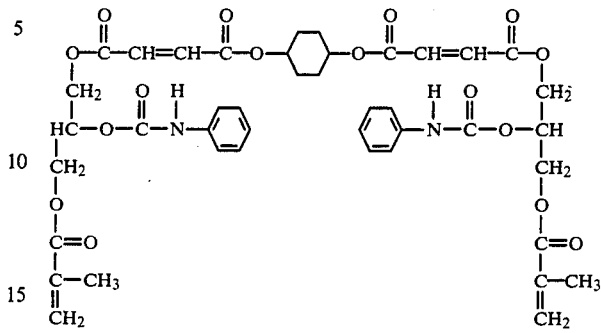

The product is solid at room temperature.

EXAMPLE D (a) In the same way as described in Example A. (a), 1,4-butylenebis [2'-(3'-methacroyl-2"-hydroxypropyl)phthalate] was prepared from 1,4-butanediol, phthalic anhydride, and glycidyl methacrylate:

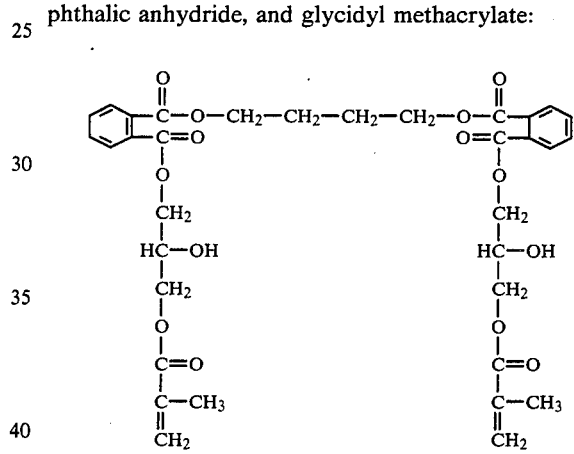

Refraction index (30° C.): 1.522.

Similarly prepared were the corresponding acrylic compounds.

(b) The product may be converted to the corresponding n-butyl, n-phenyl, n-hexyl, or cylohexyl mono- and dicarbamates. For example, this product was converted to the corresponding di n-butyl carbamate by reaction with n-butyl isocyanate as described in Example B. (b):

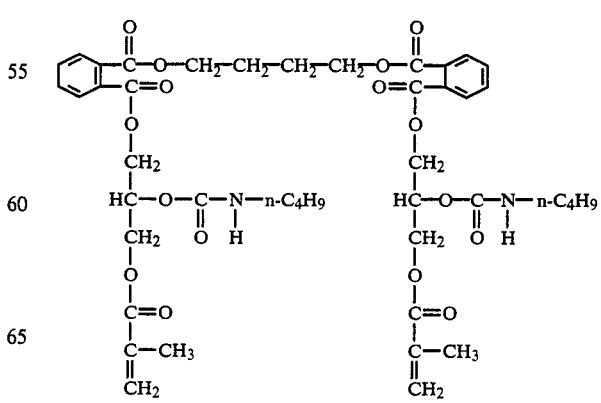

Refraction index (30° C.): 1.522

Similarly prepared were the corresponding acrylic compounds.

EXAMPLE E (a) According to the procedure described in example A. (a), from norbornene-2,3-dicarboxylic acid anhydride, 1,2-propylene glycol, and glycidyl methacrylate 1,2-propylenebis-[(3'-methacroyl-2'-hydroxypropyl)-5-norbornene-2,3-dicarboxylate] was prepared:

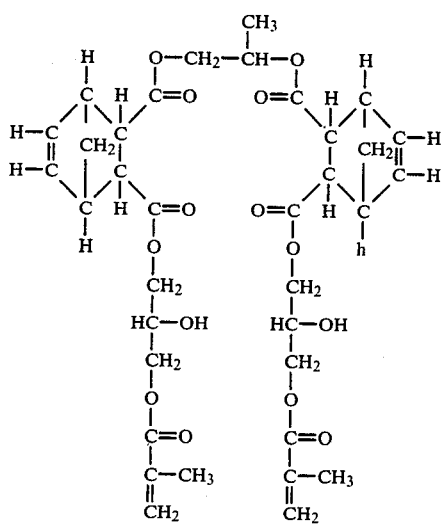

EXAMPLE F

From maleic anhydride, 4,8-bis(hydroxymethyl)-tricyclo[5.2.1.0$^{2,6}$] decane, and glycidyl methacrylate 4,8-bis [(3'-methacroyl-2'-hydroxypropyl)maleato methyl] tricyclo [5.2.1.0$^{2,6}$] decane was prepared according to the procedure outlined in Example A. (a):

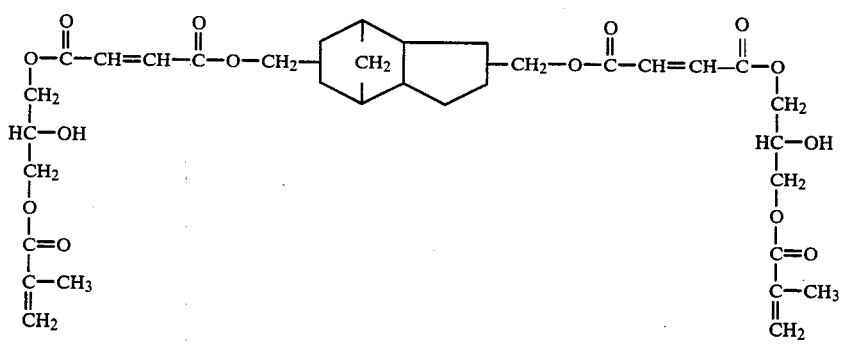

EXAMPLE G 4,8-Bis [(3'-methacroyl-2'-hydroxypropyl)-phthalatomethyl] tricyclo [5.2.1.0$^{2,6}$] decane was prepared from phthalic anhydride, 4,8-bis (hydroxymethyl)-tricyclo [5.2.1.0.$^{2,6}$] decane, and glycidyl methacrylate according to the method described in Example A. (a):

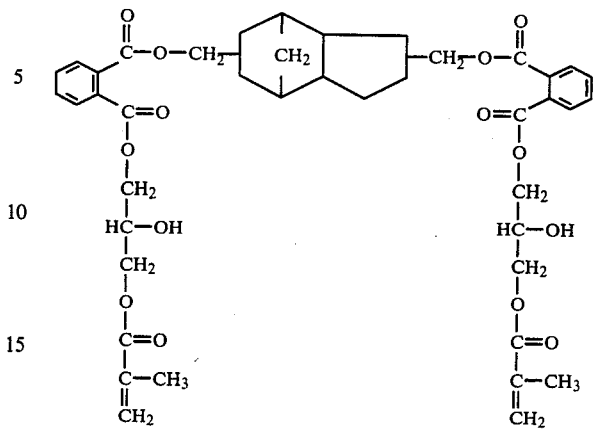

Refraction index (50° C.): 1.530

EXAMPLE H 4,8-Bis [(3'-methacroyl-2'-hydroxypropyl)cyclohexylcarboxymethyl tricyclo [5.2.1.0$^{2,6}$] decane was prepared from cyclohexane 1,2-dicarboxylic acid anhydride, 4,8-bis(hydroxymethyl) tricyclo [5.2.1.0.$^{2,6}$] decane, and glycidyl methacrylate according to the method described in Example A. (a):

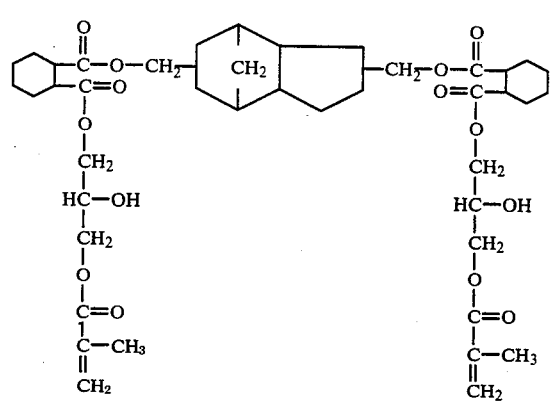

Refraction index (50° C.): 1.500

It is to be understood that, according to the same procedures, corresponding dimethacrylates and diacrylates and their carbamates mentioned in the introduction of the description and the explanation of the general formula may be prepared and used. Illustrative examples for the use of the new monomers in dental products:

Example 1

|  | Part A | Part B |
|---|---|---|
|  | (parts by weight) | |
| Compound from Example G | 70 | 70 |
| Triethyleneglycol dimethacrylate | 30 | 30 |
| Bis(tert.-butyl) p-hydroxytoluene | 0,08 | 0,08 |
| 2-Hydroxy-4-methoxybenzophenone | 0,5 | 0,5 |
| Benzoyl peroxide | — | 2,0 |
| N,N—(2-hydroxyethyl) p-toluidine | 3,5 | — |
| Hydrophobized barium borosilicate glass (Average particle size ~5-10 microns) | 600 | 600 |
| Hydrophobized fumed silica (Average particle size ~25-50 millimicrons) | 50 | 50 |

Part A & B were mixed together and cured within 120 seconds at 23° C. The cured material had translucency and other optical characteristics resembling those of the human tooth structure. Its other properties were as follows:

| Diametral tensile strength | 7200 psi (49.6 MPa) |
|---|---|
| Hardness (Barcol) | 99 |
| Water Sorption | 0.6 mg/cm$^2$ |
| Light-induced discoloration | Passed test according to ADA Specification No. 27 |

Example 2

|  | Part A | Part B |
|---|---|---|
|  | (parts by weight) | |
| 2,2-bis [4'(2"-methacroylethyloxy) phenyl]propane | 30 | 30 |
| Triethyleneglycol dimethacrylate | 19 | 19 |
| Product of Example E | 50 | 50 |
| Hydrophobized barium borosilicate glass (Average particle size ~10 microns) | 600 | 600 |
| Hydrophobized silica (Average particle size ~25-50 millimicrons) | 85 | 45 |
| Bis(tert.-butyl)p-hydroxy toluene | — | 0,10 |
| 2-hydroxy-4-methoxy benzophenone | 0,5 | 0,5 |
| Benzoyl peroxide |  | 2 |
| N,N—bis(diethanolo)-p-toluidine | 4 |  |

For curing, equal amounts of A and B were mixed and polymerized at 23° C. for 150 seconds.

The resulting polymer showed the following properties:

| Translucency factor (C$_{70}$): | 0,45 |
|---|---|
| Diametral tensile strength: | 7.000 psi |
| Water sorption: | 0,63 mg/cm$^2$ |
| Hardness (Barcol): | 99 |

Example 3

|  | Part A | Part B |
|---|---|---|
|  | (parts by weight) | |
| 2,2-bis [4'(2"-methacroylethyloxy) phenyl]propane | 56 | 56 |
| 2,2-bis [4'(3"-methacroyl-2"-hydroxy-propoxy)phenyl]propane | 10 | 10 |
| Triethyleneglycol dimethacrylate | 19 | 19 |
| Product of Example C.a) | 15 | 15 |
| 2-hydroxy-4-methoxy benzophenone | 0,6 | 0,6 |
| Bis(tert.-butyl)p-hydroxy toluene | 0,03 | 0,12 |
| N,N—bis(diethanolo)-p-toluidine | 4 |  |
| Benzoyl peroxide |  | 2 |
| Hydrophobized barium borosilicate glass (Average particle size ~10 microns) | 600 | 600 |
| Hydrophobized silica (Average particle size ~25-50 millimicrons) | 40 | 40 |

For curing, equal amounts of A and B were mixed and polymerized at 23° C. for 150 seconds.

The resulting polymer showed the following properties:

| Translucency factor (C$_{70}$): | 0,45 |
|---|---|
| Diametral tensile strength: | 5.900 psi |
| Water sorption: | 0,56 mg/cm$^2$ |
| Hardness (Barcol): | 97 |

Example 4

|  | Part A | Part B |
|---|---|---|
|  | (parts by weight) | |
| Triethyleneglycol dimethacrylate | 20 | 20 |
| Product of Example A.a) | 80 | 80 |
| 2-hydroxy-4-methoxy benzophenone | 0,5 | 0,5 |
| Bis(tert.-butyl)p-hydroxy toluene |  | 0,05 |
| N,N—bis(diethanolo)-p-toluidine | 4 |  |
| Benzoyl peroxide |  | 2,1 |
| Hydrophobized barium borosilicate glass (Average particle size ~5-15 microns) | 600 | 600 |
| Hydrophobized silica (Average particle size ~20-50 millimicrons) | 30 | 30 |

For curing, equal amounts of A and B were mixed and polymerized at 23° C. for 150 seconds.

The resulting polymer showed the following properties:

| Translucency factor (C$_{70}$): | 0,45 |
|---|---|
| Diametral tensile strength: | 6.950 psi |
| Water sorption: | 0,69 mg/cm$^2$ |
| Hardness (Barcol): | 99 |

Example 5

|  | Part A | Part B |
|---|---|---|
|  | (parts by weight) | |
| 2,2-Bis [4'(2"-methacroylethyloxy) phenyl]propane | — | 56 |
| Triethyleneglycol dimethacrylate | 20 | 19 |
| Product of Example A.b) | 80 | 25 |
| 2-hydroxy-4-methoxybenzophenone | 0,5 | 0,5 |
| Bis(tert.-butyl)-p-hydroxytoluene |  | 0,05 |
| N,N—bis(diethanolo)-p-toluidine | 3,7 |  |
| Benzoyl peroxide |  | 2,2 |
| Hydrophobized barium borosilicate glass (Average particle size ~5-10 microns) | 600 | 600 |
| Hydrophobized silica (Average particle size | 50 | 50 |

Example 5

| | Part A | Part B |
|---|---|---|
| | (parts by weight) | |
| ~25–50 millimicrons) | | |

For curing, equal amounts of A and B were mixed and polymerized at 23° C. for 150 seconds.

The resulting polymer showed the following properties:

| | |
|---|---|
| Translucency factor ($C_{70}$): | 0,47 |
| Diametral tensile strength: | 7.200 psi |
| Water sorption: | 0,65 mg/cm$^2$ |
| Hardness (Barcol): | 99 |

Example 6

| | Part A | Part B |
|---|---|---|
| | (parts by weight) | |
| Triethyleneglycoldimethacrylate | 20 | 20 |
| Product of Example H | 80 | 80 |
| Bis(tert-butyl)p-hydroxytoluene | — | 0,05 |
| Benzoyl peroxide | — | 2 |
| N,N—bis(diethanolo)p-toluidine | 3,5 | — |
| 2-Hydroxy-4-methoxybenzophenone | 0,5 | 0,5 |
| Hydrophobized quartz glass (Average particle size ~5 microns) | 600 | 600 |
| Hydrophobized silica (Average particle size ~20–40 millimicrons) | 10 | — |

For curing, equal amounts of A and B were mixed and polymerized at 23° C. for 150 seconds.

The resulting polymer showed the following properties:

| | |
|---|---|
| Translucency factor ($C_{70}$): | 0,40 |
| Diametral tensile strength: | 7.560 psi |
| Water sorption: | 0,61 mg/cm$^2$ |
| Hardness (Barcol): | 99–100 |

Example 7

| | Part A | Part B |
|---|---|---|
| | (parts by weight) | |
| 2,2-Bis [4'(3"-methacroyl-2"-hydroxypropoxy)phenyl]propane | — | 10 |
| Triethyleneglycol dimethacrylate | 20 | 20 |
| Product of Example B.b) | 80 | 70 |
| 2-hydroxy-4-methoxybenzophenone | 0,5 | 0,5 |
| Bis(tert.-butyl)-p-hydroxytoluene | — | 0,05 |
| N,N—bis(diethanolo)-p-toluidine | 3,8 | — |
| Benzoyl peroxide | | 2,2 |
| Hydrophobized barium borosilicate glass (Average particle size ~5–10 microns | 600 | 600 |
| Hydrophobized silica (Average particle size ~20–50 millimicrons) | 50 | 10 |

For curing, equal amounts of A and B were mixed and polymerized at 23° C. for 150 seconds.

The resulting polymer showed the following properties:

| | |
|---|---|
| Translucency factor ($C_{70}$): | 0,45 |
| Diametral tensile strength: | 6.700 psi |
| Water sorption: | 0,55 mg/cm$^2$ |
| Hardness (Barcol): | 99 |

Example 8

| | Part A | Part B |
|---|---|---|
| | (parts by weight) | |
| 2,2-Bis [4'(3"-methacroyl-2"-hydroxypropoxy)phenyl]propane | — | 10 |
| Triethyleneglycol dimethacrylate | 10 | 20 |
| Product of Example D.a) | 60 | 40 |
| Methylenebisphenyl carbamate of 2-methacroylethyl-, 3-methacroyl-2-hydroxypropyl(tetrahydrophthalate) | 30 | 20 |
| 2-hydroxy-4-methoxybenzophenone | 0,5 | 0,5 |
| Bis(tert.-butyl)-p-hydroxytoluene | | 0,05 |
| N,N—bis(diethanolo)-p-toluidine | 3,5 | |
| Benzoyl peroxide | | 1,8 |
| Hydrophobized barium borosilicate glass (Average particle size ~5–10 microns | 600 | 600 |
| Hydrophobized silica (Average particle size ~20–50 millimicrons) | 40 | 40 |

For curing, equal amounts of A and B were mixed and polymerized at 23° C. for 150 seconds.

The resulting polymer showed the following properties:

| | |
|---|---|
| Translucency factor ($C_{70}$): | 0,5 |
| Diametral tensile strength: | 6.300 psi |
| Water sorption: | 0,59 mg/cm$^2$ |
| Hardness (Barcol): | 99 |

Example 9

| | Part A | Part B |
|---|---|---|
| | (parts by weight) | |
| 2,2-Bis [4'(3"-methacroyl-2"-hydroxypropoxy)phenyl]propane | 10 | — |
| 1,6-Hexanediol dimethacrylate | — | 10 |
| Triethyleneglycol dimethacrylate | 10 | 10 |
| Product of Example A.b) | 80 | 80 |
| 2-hydroxy-4-methoxybenzophenone | 0,5 | 0,5 |
| Bis(tert.-butyl)-p-hydroxytoluene | | 0,05 |
| N,N—bis(diethanolo)-p-toluidine | 3,3 | |
| Benzoyl peroxide | | 1,8 |
| Hydrophobized quartz glass (Average particle size ~5–10 microns) | 600 | 600 |
| Hydrophobized silica (Average particle size ~20–50 millimicrons) | 50 | 50 |

For curing, equal amounts of A and B were mixed and polymerized at 23° C. for 150 seconds.

The resulting polymer showed the following properties:

| | |
|---|---|
| Translucency factor ($C_{70}$): | 0,5 |
| Diametral tensile strength: | 7.800 psi |
| Water sorption: | 0,63 mg/cm$^2$ |
| Hardness (Barcol): | 99–100 |

Example 10

| Product of Example F | 30 (parts by weight) |
| --- | --- |
| 2,2-Bis [4'-("-methacroyl-2"-hydroxy-propoxy)phenyl]propane | 25 |
| 1,6 Hexanediol dimethacrylate | 15 |
| Triethyleneglycol dimethacrylate | 15 |
| 4,4'-Oxydibenzil | 0,8 |
| Dimethylaminethyl methacrylate | 1,2 |
| Dimethyl p-toluidine | 0,5 |
| Hydrophobized colloidal silica (Average particle size ~40 millimicrons) | 1.15 |

The mixture is light-curable with good depth of cure and after hardening is showing excellent mechanical values and high polishability.

In the following an example for a UV hardening dental laquer is given:

| Product of Example B.a) | 14,5% by weight |
| --- | --- |
| 2-Ethylhexyl methacrylate | 25,5% |
| Ethyleneglycol dimethacrylate | 23,0% |
| 1,6-Hexanediol dimethacrylate | 30,0% |
| Acetophenone | 1,0% |
| N,N—Di(2-hydroxyethyl)p-toluidine | 1,0% |

We claim:

1. A dental restorative and/or filling material comprising at least one inorganic filler, at least one polymerization initiator, at least one polymerization accelerator and at least one diacrylic or dimethacrylic acid ester of the general formula

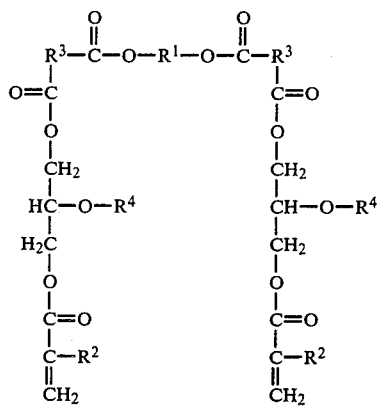

wherein $R^1$ is a divalent araliphatic, cycloaliphatic or aromatic group having 2 to 18 carbon atoms; $R^2$ is hydrogen or methyl; $R^3$ is —CH=CH— or —(CH$_2$)$_n$— wherein n is 2 to 4, substituted, unsubstituted, or hydrogenated benzene group, cyclohexylene, or cis-norbornylene; and $R^4$ is —CO—NH—$R^5$, wherein $R^5$ is n-butyl, isobutyl, hexyl, substituted or unsubstituted phenyl or cyclohexyl.

2. A dental restorative and/or filling material comprising at least one inorganic filler, at least one polymerization initiator, at least one polymerization accelerator and at least one diacrylic or dimethacrylic acid ester of the general formula

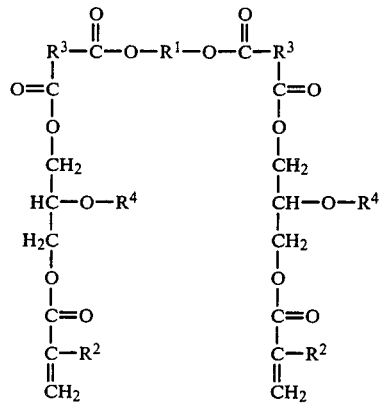

wherein $R^1$ is a divalent araliphatic, monocycloaliphatic, dicycloaliphatic or aromatic group having 2 to 18 carbon atoms; $R^2$ is hydrogen or methyl; $R^3$ is a —CH=CH— or —(CH$_2$)$_n$— wherein n is 2 to 4, substituted, unsubstituted or hydrogenated benzene group, a cyclohexylene, or cis-norbornylene; and $R^4$ is —CO—NH—$R^5$, wherein $R^5$ is n-butyl, isobutyl, hexyl, substituted or unsubstituted phenyl or cyclohexyl.

3. A dental restorative and/or filling material comprising at least one inorganic filler, at least one polymerization initiator, at least one polymerization accelerator and at least one diacrylic or dimethacrylic acid ester of the general formula

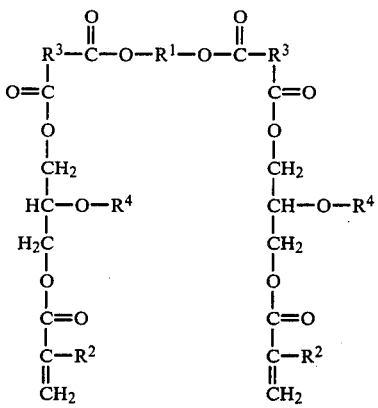

wherein $R^1$ is a ethylene, propylene, butylene, hexamethylene, phenylene, toluylene, methylene bisphenyl, propylene bisphenyl, cyclohexylene, dicyclopentyl dimethylene, methylene biscyclohexyl, and propylene biscyclohexyl; $R^2$ is hydrogen or methyl; $R^3$ is a —CH=CH— or —(CH$_2$)$_n$— wherein n is 2 to 4, a substituted unsubstituted or hydrogenated benzene group, cyclohexylene, or cis-norbornylene; and $R^4$ is —CO—NH—$R^5$, wherein $R^5$ is n-butyl, isobutyl, hexyl, substituted or unsubstituted phenyl or cyclohexyl.

* * * * *